(12) United States Patent
Thaler et al.

(10) Patent No.: US 12,286,387 B2
(45) Date of Patent: Apr. 29, 2025

(54) PROCESS OF MAKING FLUOROOLEFINS BY THERMAL DECOMPOSITION OF FLUORINATED IONOMERS

(71) Applicant: 3M INNOVATIVE PROPERTIES COMPANY, St. Paul, MN (US)

(72) Inventors: Arne Thaler, Emmerting (DE); Achim Schmidt-Rodenkirchen, Bayreuth (DE); Mark W. Muggli, Emmerting (DE); Konstantin Mierdel, Bayreuth (DE); Klaus Hintzer, Kastl (DE); Thorsten Gerdes, Eckersdorf (DE); Denis Duchesne, Woodbury, MN (US); Gregg D. Dahlke, St. Paul, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 533 days.

(21) Appl. No.: 17/777,837

(22) PCT Filed: Dec. 17, 2020

(86) PCT No.: PCT/IB2020/062145
§ 371 (c)(1),
(2) Date: May 18, 2022

(87) PCT Pub. No.: WO2021/130626
PCT Pub. Date: Jul. 1, 2021

(65) Prior Publication Data
US 2023/0002297 A1   Jan. 5, 2023

Related U.S. Application Data

(60) Provisional application No. 62/952,582, filed on Dec. 23, 2019.

(51) Int. Cl.
*C07C 17/367* (2006.01)

(52) U.S. Cl.
CPC .................. *C07C 17/367* (2013.01)

(58) Field of Classification Search
CPC ...... C07C 17/367; C07C 21/185; C07C 21/18
See application file for complete search history.

(56) References Cited

U.S. PATENT DOCUMENTS

| | | |
|---|---|---|
| 3,832,411 A | 8/1974 | Arkles et al. |
| 4,349,650 A | 9/1982 | Krespan |
| 5,386,055 A | 1/1995 | Lee et al. |
| 6,255,536 B1 | 7/2001 | Worm et al. |
| 6,294,627 B1 | 9/2001 | Worm et al. |
| 6,387,570 B1 | 5/2002 | Nakamura et al. |
| 6,780,544 B2 | 8/2004 | Noh |
| 6,797,913 B2 | 9/2004 | Van Der Walt |
| 7,252,744 B2 | 8/2007 | Van Der Walt et al. |
| 7,575,534 B2 | 8/2009 | Gleasman et al. |
| 8,212,091 B2 | 7/2012 | Van Der Walt et al. |
| 8,344,190 B2 | 1/2013 | Hintzer et al. |
| 8,367,267 B2 | 2/2013 | Frey et al. |
| 8,628,871 B2 | 1/2014 | Frey et al. |
| 9,139,496 B2 | 9/2015 | Hintzer et al. |
| 2004/0107869 A1 | 6/2004 | Velamakanni et al. |
| 2010/0311906 A1 | 12/2010 | Lavallee et al. |
| 2011/0184214 A1 | 7/2011 | Hintzer et al. |
| 2019/0027769 A1 | 1/2019 | Dahlke et al. |

FOREIGN PATENT DOCUMENTS

| | | |
|---|---|---|
| CN | 102216246 A | 10/2011 |
| CN | 108779209 A | 11/2018 |
| EP | 1481957 A1 | 12/2004 |
| EP | 1966291 B1 | 4/2009 |
| JP | H 09-501458 A | 2/1997 |
| WO | 2018211457 A2 | 11/2018 |

OTHER PUBLICATIONS

International Search Report for PCT Application No. PCT/IB2020/062145, mailed on Mar. 8, 2021, 4 pages.

Surowiec, "Studies on the Thermal Stability of the Perfluorinated Cation-exchange Membrane Nafion-417", Journal of Thermal Analysis, 1988, vol. 33, pp. 1097-1102, XP055790060.

Feng, et al., Characterization of the thermolysis products of Nafion membrane: A potential source of perfluorinated compounds in the environment, Scientific Reports, May 7, 2015, vol. 5, Article No. 9859, pp. 1-8.

*Primary Examiner* — Jafar F Parsa

(74) *Attorney, Agent, or Firm* — Julie Lapos-Kuchar; Kathleen Gross

(57) ABSTRACT

The process produces a fluorinated olefin from a fluorinated copolymer having at least one of sulfonic acid groups, carboxylic acid groups, or salts thereof. The process includes heating the fluorinated copolymer at a first temperature not more than 450° C. to decompose at least one of the sulfonic acid groups, carboxylic acid groups, or salts thereof to form a partially pyrolyzed intermediate and subsequently heating the partially pyrolyzed intermediate at a second temperature of at least 550° C. to produce the fluorinated olefin.

18 Claims, No Drawings

PROCESS OF MAKING FLUOROOLEFINS BY THERMAL DECOMPOSITION OF FLUORINATED IONOMERS

CROSS-REFERENCE TO RELATED APPLICATION

This application claims priority to U.S. Provisional Application No. 62/952,582, filed Dec. 23, 2019, the disclosure of which is incorporated by reference in its entirety herein.

BACKGROUND

Fluorinated olefins, in particular tetrafluoroethylene (TFE), are important raw materials for the preparation of fluoropolymers. TFE is commonly prepared from fluorine- and chlorine-containing starting materials (e.g. R-22=$CHClF_2$), which are of environmental concern, for example, for their potential effect on ozone depletion in the atmosphere. Therefore, there exists a need for alternative ways of producing TFE.

TFE and other fluorinated olefins are known to be derivable from thermal decomposition (pyrolysis) of fluoropolymers, such as polytetrafluoroethylene.

Several technologies for pyrolyzing fluoropolymers have been described, for example pyrolysis by steam (U.S. Pat. No. 3,832,411 (Arkles et al.)), by radio frequencies (U.S. Pat. No. 6,797,913 (Van der Walt et al.)), or by electric arcs (U.S. Pat. No. 7,252,744 (Van der Walt et al.)). U.S. Pat. No. 8,212,091 (Van der Walt et al.) discloses a process for depolymerizing fluoropolymers in a cylindrical reactor having a first reaction zone and optionally a second reaction zone. U.S. Pat. No. 8,344,190 (Hintzer et al.) discloses thermally decomposing fluoropolymers in contact with microwave particles.

SUMMARY

Fluorinated ionomers are widely used in many applications: membrane electrode assemblies in fuel cells, redox-flow batteries, and NaCl/HCl-electrolysis cells. For many industries in which these devices are used (e.g. automotive industry), it is desirable to establish a feasible recycling technology to recover as much as possible of the valuable fluorinated compounds and other materials (e.g., precious metals).

The present disclosure provides a process for producing a fluorinated olefin from a fluorinated ionomer, in some embodiments resulting in unexpectedly higher yields than other pyrolysis processes. The process can be useful, for example, for recycling ionomers from a variety of devices.

In one aspect, the present disclosure provides a process for producing a fluorinated olefin from a fluorinated copolymer having at least one of sulfonic acid groups, carboxylic acid groups, or salts thereof. The process includes heating the fluorinated copolymer at a first temperature not more than 450° C. to decompose at least one of the sulfonic acid groups, carboxylic acid groups, or salts thereof to form a partially pyrolyzed intermediate and subsequently heating the partially pyrolyzed intermediate at a second temperature of at least 550° C. to produce the fluorinated olefin.

In this application:

Terms such as "a", "an" and "the" are not intended to refer to only a singular entity but include the general class of which a specific example may be used for illustration. The terms "a", "an", and "the" are used interchangeably with the term "at least one".

The phrase "comprises at least one of" followed by a list refers to comprising any one of the items in the list and any combination of two or more items in the list. The phrase "at least one of" followed by a list refers to any one of the items in the list or any combination of two or more items in the list.

"Alkyl group" and the prefix "alk-" are inclusive of both straight chain and branched chain groups and of cyclic groups. Unless otherwise specified, alkyl groups herein have up to 20 carbon atoms. Cyclic groups can be monocyclic or polycyclic and, in some embodiments, have from 3 to 10 ring carbon atoms.

The terms "aryl" and "arylene" as used herein include carbocyclic aromatic rings or ring systems, for example, having 1, 2, or 3 rings and optionally containing at least one heteroatom (e.g., O, S, or N) in the ring optionally substituted by up to five substituents including one or more alkyl groups having up to 4 carbon atoms (e.g., methyl or ethyl), alkoxy having up to 4 carbon atoms, halo (i.e., fluoro, chloro, bromo or iodo), hydroxy, or nitro groups. Examples of aryl groups include phenyl, naphthyl, biphenyl, fluorenyl as well as furyl, thienyl, pyridyl, quinolinyl, isoquinolinyl, indolyl, isoindolyl, triazolyl, pyrrolyl, tetrazolyl, imidazolyl, pyrazolyl, oxazolyl, and thiazolyl.

"Alkylene" is the multivalent (e.g., divalent or trivalent) form of the "alkyl" groups defined above. "Arylene" is the multivalent (e.g., divalent or trivalent) form of the "aryl" groups defined above.

"Arylalkylene" refers to an "alkylene" moiety to which an aryl group is attached. "Alkylarylene" refers to an "arylene" moiety to which an alkyl group is attached.

The terms "perfluoro" and "perfluorinated" refer to groups in which all C—H bonds are replaced by C—F bonds.

The phrase "interrupted by at least one —O— group", for example, with regard to a perfluoroalkyl or perfluoroalkylene group refers to having part of the perfluoroalkyl or perfluoroalkylene on both sides of the —O— group. For example, —$CF_2CF_2$—O—$CF_2$—$CF_2$— is a perfluoroalkylene group interrupted by an —O—.

All numerical ranges are inclusive of their endpoints and nonintegral values between the endpoints unless otherwise stated (e.g., 1 to 5 includes 1, 1.5, 2, 2.75, 3, 3.80, 4, 5, etc.).

DETAILED DESCRIPTION

We have found that the pyrolysis of a fluorinated ionomer using a process reported useful for pyrolyzing polytetrafluoroethylene (PTFE) provides only about a 20% yield of tetrafluoroethylene (TFE) and hexafluoropropylene (HFE) along with multiple side products, including sulfur-containing compounds. Thus, recycling ionomers using this process is not desirable. The present disclosure provides a process for producing a fluorinated olefin from a fluorinated ionomer, in some embodiments resulting in unexpectedly higher yields than other pyrolysis processes.

The present disclosure provides a process for producing a fluorinated olefin from a fluorinated copolymer having at least one of sulfonic acid groups, carboxylic acid groups, or salts thereof. Such fluorinated copolymers are typically referred to as ionomers. In some embodiments, the fluorinated copolymer useful in the process of the present disclosure has sulfonic acid (i.e., —$SO_3H$) groups or carboxylic acid (—COOH) groups. In some embodiments, the fluorinated copolymer useful in the process of the present disclosure has —$SO_3H$ groups.

In some embodiments, the fluorinated copolymer useful in the process of the present disclosure includes divalent units represented by formula —[$CF_2$—$CF_2$]—. In some embodiments, the fluorinated copolymer comprises at least 60 mole % of divalent units represented by formula —[$CF_2$—$CF_2$]—, based on the total moles of divalent units. In some embodiments, the fluorinated copolymer comprises at least 65, 70, 75, 80, or 90 mole % of divalent units represented by formula —[$CF_2$—$CF_2$]—, based on the total moles of divalent units. Divalent units represented by formula —[$CF_2$—$CF_2$]— are incorporated into the fluorinated copolymer by copolymerizing components including tetrafluoroethylene (TFE). In some embodiments, the components to be polymerized include at least 60, 65, 70, 75, 80, or 90 mole % TFE, based on the total moles of components to be polymerized.

In some embodiments, the fluorinated copolymer useful in the process of the present disclosure includes at least one divalent unit independently represented by formula:

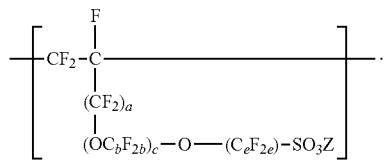

In this formula, a is 0 to 2, b is a number from 2 to 8, c is a number from 0 to 2, and e is a number from 1 to 8. In some embodiments, a is 0 or 1. In some embodiments, b is a number from 2 to 6 or 2 to 4. In some embodiments, b is 2. In some embodiments, e is a number from 1 to 6 or 2 to 4. In some embodiments, e is 2. In some embodiments, e is 4. In some embodiments, c is 0 or 1. In some embodiments, c is 0. In some embodiments, c is 0, and e is 2 or 4. In some embodiments, c is 0, and e is 3 to 8, 3 to 6, 3 to 4, or 4. In some embodiments, at least one of c is 1 or 2 or e is 3 to 8, 3 to 6, 3 to 4, or 4. In some embodiments, when a and c are 0, then e is 3 to 8, 3 to 6, 3 to 4, or 4. In some embodiments, b is 3, c is 1, and e is 2. In some embodiments, b is 2 or 3, c is 1, and e is 2 or 4. In some embodiments, a, b, c, and e may be selected to provide greater than 2, at least 3, or at least 4 carbon atoms. $C_bF_{2b}$ and $C_eF_{2e}$ may be linear or branched. In some embodiments, $C_eF_{2e}$ can be written as $(CF_2)_e$, which refers to a linear perfluoroalkylene group. When c is 2, the b in the two $C_bF_{2b}$ groups may be independently selected. However, within a $C_bF_{2b}$ group, a person skilled in the art would understand that b is not independently selected. In any of these embodiments, each Z is independently a hydrogen, alkyl having up to 4, 3, 2, or 1 carbon atoms, an alkali metal cation, or a quaternary ammonium cation. The quaternary ammonium cation can be substituted with any combination of hydrogen and alkyl groups, in some embodiments, alkyl groups independently having from one to four carbon atoms. In some embodiments, Z is an alkali-metal cation. In some embodiments, Z is a sodium or lithium cation. In some embodiments, Z is a sodium cation. In some embodiments, Z is hydrogen.

Fluorinated copolymers having divalent units represented by this formula can be prepared, for example, by copolymerizing components including at least one polyfluoroalkyloxy or polyfluorovinyloxy compound represented by formula $CF_2$=$CF(CF_2)_a$—$(OC_bF_{2b})_c$—O—$(C_eF_{2e})$—$SO_2X''$, in which a, b, c, and e are as defined above in any of their embodiments, and each $X''$ is independently —F or —OZ. Hydrolysis of a copolymer having —$SO_2F$ groups with an alkaline hydroxide (e.g. LiOH, NaOH, or KOH) solution provides —$SO_3Z$ groups, which may be subsequently acidified to $SO_3H$ groups. Treatment of a copolymer having —$SO_2F$ groups with water and steam can form $SO_3H$ groups. Suitable polyfluoroalkyloxy and polyfluorovinyloxy compounds include $CF_2$=$CFCF_2$—O—$CF_2$—$SO_2X''$, $CF_2$=$CFCF_2$—O—$CF_2CF_2$—$SO_2X''$, $CF_2$=$CFCF_2$—O—$CF_2CF_2CF_2$—$SO_2X''$, $CF_2$=$CFCF_2$—O—$CF_2CF_2CF_2CF_2$—$SO_2X''$, $CF_2$=$CFCF_2$—O—$CF_2CF(CF_3)$—O—$(CF_2)_e$—$SO_2X''$, $CF_2$=$CF$—O—$CF_2$—$SO_2X''$, $CF_2$=$CF$—O—$CF_2CF_2$—$SO_2X''$, $CF_2$=$CF$—O—$CF_2CF_2CF_2$—$SO_2X''$, $CF_2$=$CF$—O—$CF_2CF_2CF_2CF_2$—$SO_2X''$, and $CF_2$=$CF$—O—$CF_2$—$CF(CF_3)$—O—$(CF_2)_e$—$SO_2X''$. In some embodiments, the compound represented by formula $CF_2$=$CF(CF_2)_a$—$(OC_bF_{2b})_c$—O—$(C_eF_{2e})$—$SO_2X''$ is $CF_2$=$CFCF_2$—O—$CF_2CF_2$—$SO_2X''$, $CF_2$=$CF$—O—$CF_2CF_2$—$SO_2X''$, $CF_2$=$CFCF_2$—O—$CF_2CF_2CF_2CF_2$—$SO_2X''$, or $CF_2$=$CF$—O—$CF_2CF_2CF_2CF_2$—$SO_2X''$. Compounds represented by formula $CF_2$=$CF(CF_2)_a$—$(OC_bF_{2b})_c$—O—$(C_eF_{2e})$—$SO_2X''$ can be made by known methods.

In some embodiments, the fluorinated copolymer useful in the process of the present disclosure includes at least one divalent unit independently represented by formula:

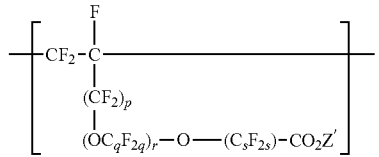

wherein p is 0 to 2, q is 2 to 8, r is 0 to 2, s is 1 to 8, and Z' is a hydrogen, an alkali-metal cation, or a quaternary ammonium cation. In some embodiments, p is 0 or 1. In some embodiments, q is a number from 2 to 6 or 2 to 4. In some embodiments, q is 2. In some embodiments, s is a number from 1 to 6 or 2 to 4. In some embodiments, s is 2. In some embodiments, s is 4. In some embodiments, r is 0 or 1. In some embodiments, r is 0. In some embodiments, r is 0, and s is 2 or 4. In some embodiments, q is 3, r is 1, and s is 2. $C_qF_{2q}$ and $C_sF_{2s}$ may be linear or branched. In some embodiments, $C_sF_{2s}$ can be written as $(CF_2)_s$, which refers to a linear perfluoroalkylene group. When r is 2, the q in the two $C_qF_{2q}$ groups may be independently selected. However, within a $C_qF_{2q}$ group, a person skilled in the art would understand that q is not independently selected. Each Z' is independently a hydrogen, alkyl having up to 4, 3, 2, or 1 carbon atoms, an alkali metal cation, or a quaternary ammonium cation. The quaternary ammonium cation can be substituted with any combination of hydrogen and alkyl groups, in some embodiments, alkyl groups independently having from one to four carbon atoms. In some embodiments, Z' is an alkali-metal cation. In some embodiments, Z' is a sodium or lithium cation. In some embodiments, Z' is a sodium cation. In some embodiments, Z' is hydrogen. Fluorinated copolymers having divalent units represented by this formula can be prepared, for example, by copolymerizing components including at least one polyfluoroalkyloxy or polyfluorovinyloxy compound represented by formula $CF_2$=$CF(CF_2)_p$—$(OC_qF_{2q})_r$—O—$(C_sF_{2s})$—$COOZ'$, in which p, q, r, s, and Z' are as defined above in any of their embodiments, The fluorinated copolymer useful in the process of the present disclosure can have an —$SO_3Z$ or —$CO_2Z'$ equivalent weight of up to 2000, 1900, 1800, or 1750. In some embodiments, the copolymer has an —SO$_3$Z or —CO$_2$Z' equivalent weight of at least 500, 600, 700, 800, 900, 950, or 1000. In some embodiments, the copolymer has an —SO$_3$Z or —CO$_2$Z' equivalent weight in a range from 500 to 2000, 800 to 2000, 950 to 2000, or 1000 to 2000. In general, the —SO$_3$Z or —CO$_2$Z' equivalent weight of the copolymer refers to the weight of the copolymer containing one mole of —SO$_3$Z or —CO$_2$Z' groups, wherein Z and Z' are as defined above in any of its embodiments. In some embodiments, the —SO$_3$Z or —CO$_2$Z' equivalent weight of the copolymer refers to the weight of the copolymer that will neutralize one equivalent of base. In some embodiments, the —SO$_3$Z or —CO$_2$Z' equivalent weight of the copolymer refers to the weight of the copolymer containing one mole of sulfonate groups (i.e., —SO$_3$—) or carboxylate groups (i.e., —CO$_2$—). Decreasing the —SO$_3$Z or —CO$_2$Z' equivalent weight of the copolymer tends to increase proton conductivity in the copolymer but tends to decrease its crystallinity, which may compromise the mechanical properties of the copolymer (e.g., tensile strength). Thus, the —SO$_3$Z or —CO$_2$Z' equivalent weight of the copolymer useful in the process of the present disclosure typically and advantageously provides a balance of the requirements for the electrical and mechanical properties of the copolymer.

The fluorinated copolymer useful in the process of the present disclosure can have up to 30 mole percent of divalent units represented by formula

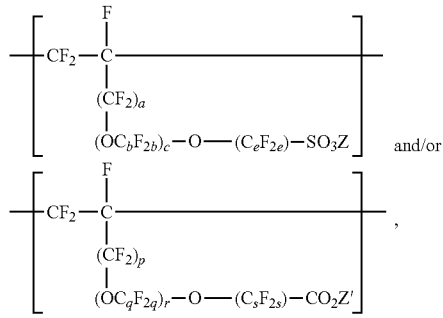 and/or based on the total amount of the divalent units. In some embodiments, the copolymer comprises up to 25 or 20 mole percent of these divalent units, based on the total amount of these divalent units. In some embodiments, the copolymer comprises at least 2, 5, or 10 mole percent of these divalent units, based on the total amount of these divalent units. The copolymer can be prepared by copolymerization components comprising up to 30 mole percent of at least one compound represented by formula $CF_2$=$CF(CF_2)_a$—$(OC_bF_{2b})_c$—O—$(C_eF_{2e})$—$SO_2X''$ or $CF_2$=$CF(CF_2)_p$—$(OC_qF_{2q})_r$—O—$(C_sF_{2s})$—COOZ', in any of their embodiments described above, based on the total amount of components that are copolymerized.

In some embodiments of the fluorinated copolymer useful in the process of the present disclosure, the fluorinated copolymer includes divalent units represented by formula

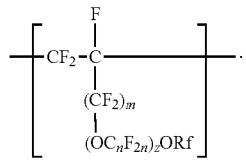

In this formula Rf is a linear or branched perfluoroalkyl group having from 1 to 8 carbon atoms and optionally interrupted by one or more —O— groups, z is 0, 1 or 2, each n is independently from 1 to 4, and m is 0 to 2. In some embodiments, m is 0 or 1. In some embodiments, n is 1, 3, or 4, or from 1 to 3, or from 2 to 3, or from 2 to 4. In some embodiments, when z is 2, one n is 2, and the other is 1, 3, or 4. In some embodiments, when a is 1 in any of the formulas described above, for example, n is from 1 to 4, 1 to 3, 2 to 3, or 2 to 4. In some embodiments, n is 1 or 3. In some embodiments, n is 1. In some embodiments, n is not 3. When z is 2, the n in the two $C_nF_{2n}$ groups may be independently selected. However, within a $C_nF_{2n}$ group, a person skilled in the art would understand that n is not independently selected. $C_nF_{2n}$ may be linear or branched. In some embodiments, $C_nF_{2n}$ is branched, for example, —$CF_2$—$CF(CF_3)$—. In some embodiments, $C_nF_{2n}$ can be written as $(CF_2)_n$, which refers to a linear perfluoroalkylene group. In these cases, the divalent units of this formula are represented by formula

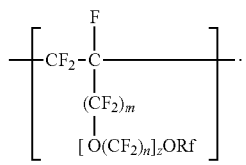

In some embodiments, $C_nF_{2n}$ is —$CF_2$—$CF_2$—$CF_2$—. In some embodiments, $(OC_nF_{2n})_z$ is represented by —O—$(CF_2)_{1-4}$—$[O(CF_2)_{1-4}]_{0-1}$. In some embodiments, Rf is a linear or branched perfluoroalkyl group having from 1 to 8 (or 1 to 6) carbon atoms that is optionally interrupted by up to 4, 3, or 2 —O— groups. In some embodiments, Rf is a perfluoroalkyl group having from 1 to 4 carbon atoms optionally interrupted by one —O— group. In some embodiments, z is 0, m is 0, and Rf is a linear or branched perfluoroalkyl group having from 1 to 4 carbon atoms. In some embodiments, z is 0, m is 0, and Rf is a branched perfluoroalkyl group having from 3 to 8 carbon atoms. In some embodiments, m is 1, and Rf is a branched perfluoroalkyl group having from 3 to 8 carbon atoms or a linear perfluoroalkyl group having 5 to 8 carbon atoms. In some embodiments, Rf is a branched perfluoroalkyl group having from 3 to 6 or 3 to 4 carbon atoms. An example of a useful perfluoroalkyl vinyl ether (PAVE) from which these divalent units in which m and z are 0 are derived is perfluoroisopropyl vinyl ether ($CF_2$=$CFOCF(CF_3)_2$), also called iso-PPVE. Other useful PAVEs include perfluoromethyl vinyl ether, perfluoroethyl vinyl ether, and perfluoropropyl vinyl ether.

Divalent units represented by formulas

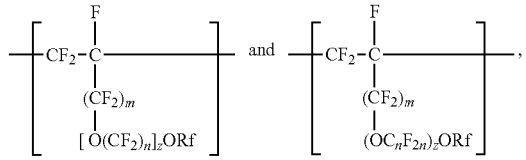

in which m is 0, typically arise from perfluoroalkoxyalkyl vinyl ethers. Suitable perfluoroalkoxyalkyl vinyl ethers (PAOVE) include those represented by formula $CF_2$=$CF$ $[O(CF_2)_n]_zORf$ and $CF_2=CF(OC_nF_{2n})_zORf$, in which n, z, and Rf are as defined above in any of their embodiments. Examples of suitable perfluoroalkoxyalkyl vinyl ethers include $CF_2=CFOCF_2OCF_3$, $CF_2=CFOCF_2OCF_2CF_3$, $CF_2=CFOCF_2CF_2OCF_3$, $CF_2=CFOCF_2CF_2CF_2OCF_3$, $CF_2=CFOCF_2CF_2CF_2CF_2OCF_3$, $CF_2=CFOCF_2CF_2OCF_2CF_3$, $CF_2=CFOCF_2CF_2CF_2OCF_2CF_3$, $CF_2=CFOCF_2CF_2CF_2CF_2OCF_2CF_3$, $CF_2=CFOCF_2CF_2OCF_2OCF_3$, $CF_2=CFOCF_2CF_2OCF_2CF_2OCF_3$, $CF_2=CFOCF_2CF_2OCF_2CF_2CF_2OCF_3$, $CF_2=CFOCF_2CF_2OCF_2CF_2CF_2CF_2OCF_3$, $CF_2=CFOCF_2CF_2OCF_2CF_2CF_2CF_2CF_2OCF_3$, $CF_2=CFOCF_2CF_2(OCF_2)_3OCF_3$, $CF_2=CFOCF_2CF_2(OCF_2)_4OCF_3$, $CF_2=CFOCF_2CF_2OCF_2OCF_2OCF_3$, $CF_2=CFOCF_2CF_2OCF_2CF_2CF_2CF_2=CFOCF_2CF_2OCF_2CF_2OCF_2CF_3$, $CF_2=CFOCF_2CF(CF_3)$—O—$C_3F_7$ (PPVE-2), $CF_2=CF(OCF_2CF(CF_3))_2$—O—$C_3F_7$(PPVE-3), and $CF_2=CF(OCF_2CF(CF_3))_3$—O—$C_3F_7$(PPVE-4). In some embodiments, the perfluoroalkoxyalkyl vinyl ether is selected from $CF_2=CFOCF_2OCF_3$, $CF_2=CFOCF_2OCF_2CF_3$, $CF_2=CFOCF_2CF_2OCF_3$, $CF_2=CFOCF_2CF_2CF_2OCF_3$, $CF_2=CFOCF_2CF_2OCF_2CF_3$, $CF_2=CFOCF_2CF_2CF_2OCF_2CF_3$, $CF_2=CFOCF_2CF_2OCF_2OCF_3$, $CF_2=CFOCF_2CF_2OCF_2CF_2OCF_3$, $CF_2=CFOCF_2CF_2OCF_2CF_2CF_2OCF_3$, $CF_2=CFOCF_2CF_2OCF_2CF_2CF_2CF_2OCF_3$, $CF_2=CFOCF_2CF_2(OCF_2)_3OCF_3$, $CF_2=CFOCF_2CF_2(OCF_2)_4OCF_3$, $CF_2=CFOCF_2CF_2OCF_2OCF_2OCF_3$, and combinations thereof. Many of these perfluoroalkoxyalkyl vinyl ethers can be prepared according to the methods described in U.S. Pat. No. 6,255,536 (Worm et al.) and 6,294,627 (Worm et al.). In some embodiments, the PAOVE is perfluoro-3-methoxy-n-propyl vinyl ether. In some embodiments, the PAOVE is other than perfluoro-3-methoxy-n-propyl vinyl ether.

The divalent units represented by formula

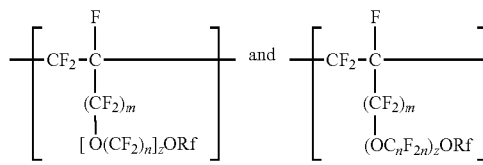

in which m is 1, are typically derived from at least one perfluoroalkoxyalkyl allyl ether. Suitable perfluoroalkoxyalkyl allyl ethers include those represented by formula $CF_2=CFCF_2(OC_nF_{2n})_zORf$, in which n, z, and Rf are as defined above in any of their embodiments. Examples of suitable perfluoroalkoxyalkyl allyl ethers include
$CF_2=CFCF_2OCF_2CF_2OCF_3$,
$CF_2=CFCF_2OCF_2CF_2CF_2OCF_3$,
$CF_2=CFCF_2OCF_2OCF_3$, $CF_2=CFCF_2OCF_2OCF_2CF_3$,
$CF_2=CFCF_2OCF_2CF_2CF_2CF_2OCF_3$,
$CF_2=CFCF_2OCF_2CF_2OCF_2CF_3$,
$CF_2=CFCF_2OCF_2CF_2CF_2OCF_2CF_3$,
$CF_2=CFCF_2OCF_2CF_2CF_2CF_2OCF_2CF_3$,
$CF_2=CFCF_2OCF_2CF_2OCF_2OCF_3$,
$CF_2=CFCF_2OCF_2CF_2OCF_2CF_2OCF_3$,
$CF_2=CFCF_2OCF_2CF_2OCF_2CF_2CF_2OCF_3$,
$CF_2=CFCF_2OCF_2CF_2OCF_2CF_2CF_2CF_2OCF_3$,
$CF_2=CFCF_2OCF_2CF_2OCF_2CF_2CF_2CF_2CF_2OCF_3$,
$CF_2=CFCF_2OCF_2CF_2(OCF_2)_3OCF_3$,
$CF_2=CFCF_2OCF_2CF_2(OCF_2)_4OCF_3$,
$CF_2=CFCF_2OCF_2CF_2OCF_2OCF_2OCF_3$,
$CF_2=CFCF_2OCF_2CF_2OCF_2CF_2CF_3$,
$CF_2=CFCF_2OCF_2CF_2OCF_2CF_2OCF_2CF_2CF_3$,
$CF_2=CFCF_2OCF_2CF(CF_3)$—O—$C_3F_7$, and $CF_2=CFCF_2(OCF_2CF(CF_3))_2$—O—$C_3F_7$. In some embodiments, the perfluoroalkoxyalkyl allyl ether is selected from
$CF_2=CFCF_2OCF_2CF_2OCF_3$,
$CF_2=CFCF_2OCF_2CF_2CF_2OCF_3$,
$CF_2=CFCF_2OCF_2OCF_3$, $CF_2=CFCF_2OCF_2OCF_2CF_3$,
$CF_2=CFCF_2OCF_2CF_2CF_2CF_2OCF_3$,
$CF_2=CFCF_2OCF_2CF_2OCF_2CF_3$,
$CF_2=CFCF_2OCF_2CF_2CF_2OCF_2CF_3$,
$CF_2=CFCF_2OCF_2CF_2CF_2CF_2OCF_2CF_3$,
$CF_2=CFCF_2OCF_2CF_2OCF_2OCF_3$,
$CF_2=CFCF_2OCF_2CF_2OCF_2CF_2OCF_3$,
$CF_2=CFCF_2OCF_2CF_2OCF_2CF_2CF_2OCF_3$,
$CF_2=CFCF_2OCF_2CF_2OCF_2CF_2CF_2CF_2OCF_3$,
$CF_2=CFCF_2OCF_2CF_2OCF_2CF_2CF_2CF_2CF_2OCF_3$,
$CF_2=CFCF_2OCF_2CF_2(OCF_2)_3OCF_3$,
$CF_2=CFCF_2OCF_2CF_2(OCF_2)_4OCF_3$,
$CF_2=CFCF_2OCF_2CF_2OCF_2OCF_2OCF_3$,
$CF_2=CFCF_2OCF_2CF_2OCF_2CF_2CF_3$,
$CF_2=CFCF_2OCF_2CF_2OCF_2CF_2OCF_2CF_2CF_3$, and combinations thereof. Many of these perfluoroalkoxyalkyl allyl ethers can be prepared, for example, according to the methods described in U.S. Pat. No. 4,349,650 (Krespan) and Int. Pat. Appl. Pub. No. WO 2018/211457 (Hintzer et al.).

The fluorinated copolymer useful in the process of the present disclosure can include divalent units derived from these vinyl ethers and allyl ethers in any useful amount, in some embodiments, in an amount of up to 20, 15, 10, 7.5, or 5 mole percent, at least 3, 4, 4.5, 5, or 7.5 mole percent, or in a range from 3 to 20, 4 to 20, 4.5 to 20, 5 to 20, 7.5 to 20, or 5 to 15 mole percent, based on the total moles of divalent units. In some embodiments, fluorinated copolymers useful in the process of the present disclosure are free of divalent units represented by formula

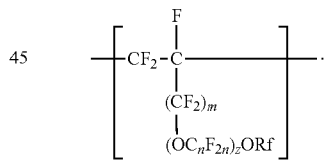

In some embodiments of the fluorinated copolymer useful in the process of the present disclosure, the copolymer includes divalent units derived from at least one fluorinated olefin independently represented by formula $C(R)_2=CF-Rf_2$. These fluorinated divalent units are represented by formula —[$CR_2$—$CFRf_2$]—. In formulas $C(R)_2=CF-Rf_2$ and —[$CR_2$—$CFRf_2$]—, $Rf_2$ is fluorine or a perfluoroalkyl having from 1 to 8, in some embodiments 1 to 3, carbon atoms, and each R is independently hydrogen, fluorine, or chlorine. Some examples of fluorinated olefins useful as components of the polymerization include, hexafluoropropylene (HFP), trifluorochloroethylene (CTFE), and partially fluorinated olefins (e.g., vinylidene fluoride (VDF), tetrafluoropropylene (R1234yf), pentafluoropropylene, and trifluoroethylene). In some embodiments, the fluorinated ionomer includes at least one of divalent units derived from chlorotrifluoroethylene or divalent units derived from hexafluoropropylene. Divalent units represented by formula —[CR$_2$—CFRf$_2$]— may be present in the fluorinated copolymer in any useful amount, in some embodiments, in an amount of up to 10, 7.5, or 5 mole percent, based on the total moles of divalent units.

Fluorinated copolymers useful for the process of the present disclosure can also include units derived from bisolefins represented by formula X$_2$C=CY—(CW$_2$)$_w$—(O)$_x$—R$_F$—(O)$_y$—(CW$_2$)$_z$CY=CX$_2$. In this formula, each of X, Y, and W is independently fluoro, hydrogen, alkyl, alkoxy, polyoxyalkyl, perfluoroalkyl, perfluoroalkoxy or perfluoropolyoxyalkyl, w and z are independently an integer from 0 to 15, and x and y are independently 0 or 1. In some embodiments, X, Y, and W are each independently fluoro, CF$_3$, C$_2$F$_5$, C$_3$F$_7$, C$_4$F$_9$, hydrogen, CH$_3$, C$_2$H$_5$, C$_3$H$_7$, C$_4$H$_9$. In some embodiments, X, Y, and W are each fluoro (e.g., as in CF$_2$=CF—O—R$_F$—O—CF=CF$_2$ and CF$_2$=CF—CF$_2$—O—R$_F$—O—CF$_2$—CF=CF$_2$). In some embodiments, n and o are 1, and the bisolefins are divinyl ethers, diallyl ethers, or vinyl-allyl ethers. R$_F$ represents linear or branched perfluoroalkylene or perfluoropolyoxyalkylene or arylene, which may be non-fluorinated or fluorinated. In some embodiments, R$_F$ is perfluoroalkylene having from 1 to 12, from 2 to 10, or from 3 to 8 carbon atoms. The arylene may have from 5 to 14, 5 to 12, or 6 to 10 carbon atoms and may be non-substituted or substituted with one or more halogens other than fluoro, perfluoroalkyl (e.g. —CF$_3$ and —CF$_2$CF$_3$), perfluoroalkoxy (e.g. —O—CF$_3$, —OCF$_2$CF$_3$), perfluoropolyoxyalkyl (e.g., —OCF$_2$OCF$_3$; —CF$_2$OCF$_2$OCF$_3$), fluorinated, perfluorinated, or non-fluorinated phenyl or phenoxy, which may be substituted with one or more perfluoroalkyl, perfluoroalkoxy, perfluoropolyoxyalkyl groups, one or more halogens other than fluoro, or combinations thereof. In some embodiments, R$_F$ is phenylene or mono-, di-, tri- or tetrafluoro-phenylene, with the ether groups linked in the ortho, para or meta position. In some embodiments, R$_F$ is CF$_2$; (CF$_2$)$_q$ wherein q is 2, 3, 4, 5, 6, 7 or 8; CF$_2$—O—CF$_2$; CF$_2$—O—CF$_2$—CF$_2$; CF(CF$_3$)CF$_2$; (CF$_2$)$_2$—O—CF(CF$_3$)—CF$_2$; CF(CF$_3$)—CF$_2$—O—CF(CF$_3$)CF$_2$; or (CF$_2$)$_2$—O—CF(CF$_3$)—CF$_2$—O—CF(CF$_3$)—CF$_2$—O—CF$_2$. The bisolefins can introduce long chain branches as described in U.S. Pat. Appl. Pub. No. 2010/0311906 (Lavallde et al.). The bisolefins, described above in any of their embodiments, may be present in the components to be polymerized in any useful amount, in some embodiments, in an amount of up to 2, 1, or 0.5 mole percent and in an amount of at least 0.1 mole percent, based on the total amount of polymerizable components to make the fluorinated copolymer.

Fluorinated copolymers useful for the process of the present disclosure can also include units derived from non-fluorinated monomers. Examples of suitable non-fluorinated monomers include ethylene, propylene, isobutylene, ethyl vinyl ether, vinyl benzoate, ethyl allyl ether, cyclohexyl allyl ether, norbornadiene, crotonic acid, an alkyl crotonate, acrylic acid, an alkyl acrylate, methacrylic acid, an alkyl methacrylate, and hydroxybutyl vinyl ether. Any combination of these non-fluorinated monomers may be useful. In some embodiments, the components to be polymerized further include acrylic acid or methacrylic acid, and the copolymer of the present disclosure includes units derived from acrylic acid or methacrylic acid.

Fluorinated copolymers useful in the process of the present disclosure are typically prepared by free-radical polymerization (e.g., radical aqueous emulsion polymerization suspension polymerization) using known methods.

Fluorinated olefins that are produced by the process of the present disclosure include olefins corresponding to the general formula:

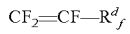

wherein R$^d_f$ represents F or a perfluoroalkyl group having 1 to 10 (in some embodiment, 1 to 5) carbon atoms. In some embodiments, the fluorinated olefin produced by the process comprises at least one of tetrafluoroethylene (TFE) or hexafluoropropylene (HFP). In some embodiments, both TFE and HFP are produced.

In the process of the present disclosure, the thermal decomposition of the fluorinated copolymer comprising at least one of sulfonic acid groups, carboxylic acid groups, or salts thereof into fluorinated olefins can be carried out in any suitable reactor capable of generating the temperature required for the decomposition reaction. For example, the thermal decomposition may be carried out in rotary kilns reactors. Rotary kiln reactors are described, for example in European Pat. Appl. EP 1 481 957 (Ichida et al.). The decomposition may also be carried out in extruder type reaction devices, for example devices as described in U.S. Pat. No. 8,212,091 (Van der Walt et al.) and agitated reactors. These devices can be operated with or without gas streams, such as carrier gases or gaseous reaction medium. In some embodiments, the decomposition is carried out in a fluidized bed reactor (see, for example, J. R. Howard, "Fluidized Bed Technology, Principles and Applications", Adam Hingler, New York, 1989). Typically, a gas or a gas mixture is used as fluidizing medium. The carrier gas or gaseous fluidizing or reaction medium typically comprises non-reactive gases (i.e. gases that do not react under the decomposition conditions in the reactor), such as steam, nitrogen, noble gases (e.g., Xe, Ar, Ne, and He), and mixtures thereof. However, in some embodiments, the carrier gas and/or medium may also contain reactive gases, i.e. fluorine-containing gases which may also decompose under the conditions in the reactor and be converted into TFE and/or HFP. The process of the present disclosure may be run as batch process or a continuous process.

Carrier gas and/or reaction or fluidizing medium can be introduced in the reactor as separate gas streams. The optimum flow rates of the carrier gas or medium depends on the configuration of the reactor, the reaction and/or process conditions. Typical flow rates lie in the range of from about 0.01 to about 1,000 reactor volumes/min, in some embodiments, from about 0.1 to about 100 reactor volumes/min. The processes may be run at a pressure of from about 0.01 bar to about 5 bar or at atmospheric pressure (1 bar). The zone of the reactor where conditions are achieved under which decomposition takes place is referred to herein as "decomposition zone" of the reactor. In some embodiments, the gas stream (e.g., carrier gas stream or fluidising gas stream) is pre-heated before introduction into the decomposition zone of the reactor. Pre-heating can be carried out to a temperature equal to the decomposition temperature or a temperature 50° C. to 200° C. below the decomposition temperature.

The process of the present disclosure includes heating the fluorinated copolymer at a first temperature not more than 450° C. to decompose the at least one of sulfonic acid groups, carboxylic acid groups, or salts thereof to form a partially pyrolyzed intermediate. In some embodiments, the first temperature is not more than 440° C., 430° C., 425° C., 420° C., 410° C., or 400° C. In some embodiments, the first temperature is in a range from 300° C. to 450° C., 350° C. to 450° C., 350° C. to 425° C., or 375° C. to 425° C. The process of the present disclosure further comprises subsequently heating the partially pyrolyzed intermediate at a second temperature of at least 550° C. to produce the fluorinated olefin. In some embodiments, the second temperature is in a range from 550° C. to 900° C., in some embodiments, from 600° C. to 900° C., 600° C. to 800° C., or 600° C. to 700° C. The first and second temperatures can be adjusted, for example, based on the composition of the fluorinated copolymer, the pressure under which the reactor is operated, the flow rate by which the fluorinated copolymer is fed through the reactor, and the time which the fluorinated copolymer remains in the decomposition zone.

The fluorinated copolymer may be heated at the first temperature for any suitable period of time to decompose the sulfonic acid groups, carboxylic acid groups, salts thereof, or combinations thereof. In some embodiments, the fluorinated copolymer is heated at the first temperature for up to two hours, 90 minutes, or one hour. The partially pyrolyzed intermediate can be heated at a second temperature for any suitable period of time to produce the fluorinated olefin. In some embodiments, the partially pyrolyzed intermediate is heated at the second temperature for up to one hour or 45, 30, 20, 10, or 5 minutes. It is possible that the yield of the fluorinated olefin may be increased if the partially pyrolyzed intermediate in is heated at the second temperature for very short time, which can be achieved, for example, in fluidized bed reactors or in reactors using gas streams to carry the fluorinated material through the decomposition zone in short time. Short retention times at the second temperature can be achieved by high flow rates of the respective gas streams. In some embodiments, the partially pyrolyzed intermediate is heated at the second temperature for at least 5 seconds and up to one minute.

In some embodiments, the fluorinated copolymer to be heated at the first temperature comprises at least one of the sulfonic acid groups (—$SO_3H$) or carboxylic acid groups (—$CO_2H$). Salts of the fluorinated copolymers (e.g. from the NaCl-electrolyzers), can be converted to the acid form by a treatment with acids such as at least one of sulfuric acid, hydrochloric acid, or HF. This will typically enhance the decomposition of the functional groups during the heating at the first temperature.

Heating at the first temperature and subsequently heating at the second temperature can be carried out in the same reactor or different reactors In some embodiments, at least one of heating at the first temperature or subsequently heating at the second temperature is carried out at least partially with microwave irradiation. The decomposition temperatures may be generated entirely by microwave irradiation or by a combination of microwave heating and conventional heating (e.g., heat exchange, combustion, or resistance heating). Therefore, in some embodiments, the reactor comprises one or more microwave generators for generating microwave radiation. Microwave-generated reactors are known in the art. The microwaves may be generated by devices such diodes, magnetrons, gyrotrons, travelling wave tubes, klystrons, ubitrons, and amplitrons, for example. Typically, the microwave generators are situated in the inside of the reactor. The inside of the reactor may be made of a material or coated with a material that increases the heating effect of the microwaves. Microwave irradiation as referred to herein means irradiation with electromagnetic waves having a wave length of about 30 cm to about 3 mm and/or a frequency band of from about 300 MHz to about 300 GHz, in some embodiments from about 915 MHz to about 2.45 GHz.

In some embodiments, at least one of the fluorinated copolymer or the partially pyrolyzed intermediate is contacted by microwave active particles, for example, while being heated at least partially with microwave radiation. The fluorinated ionomer or the partially pyrolyzed intermediate can also be contacted by microwave active particles immediately before being thermally decomposed. Typically, the particles are present in the reaction medium, for example, by feeding the particles into the decomposition zone by a carrier gas stream or in the fluidised bed of a fluidised bed reactor. Microwave active particles heat up upon irradiation by microwaves, for example, through absorption of microwaves. Typically, microwave active materials heat up by at least 10° C., at least 20° C., or at least 30° C. when submitting 1 g of the microwave active material at ambient conditions to microwave irradiation of 0.7 kW for 5 minutes.

In some embodiments, useful microwave active particles are solid at the first temperature and/or second temperature. In some embodiments, the microwave active particles have a melting point or decomposition point of at least 800° C., at least 1,000° C., or at least 1,500° C. Examples of suitable microwave active particles include carbon, graphite, carbides, silicides, borides, nitrides, metal oxides, metal hydroxides, metal halides (e.g., metal chlorides and metal fluorides), silicium carbide, boron carbides, titanium carbides, zirconium carbides, molebdenium silicides, titanium borides, sodium chloride, magnesium chlorides, potassium chloride, cobalt fluorides, potassium fluoride, calcium fluorides, and combinations thereof. Further examples of suitable microwave active particles include metals such as Ni, Pt, Co; Pt; metal alloys such as Pt/Cu, Pt/Re alloys; chromates; titanates; and combinations thereof. Combinations or blends of different microwave active particles may be useful in the process of the present disclosure. The microwave active particles can be selected such that they do not react with the reaction mixture and lose their microwave activity.

The optimum size and amounts of the particles may be adapted to the specific composition of the fluorinated copolymer, the configuration of the reactor, and the process conditions. Typically, the particles have an average particle size (number average) from about 100 µm to about 5 mm, or from about 250 µm to about 2 mm. The particles may be spherical or non-spherical. In case of spherical or substantially spherical particles, the average size is determined by measuring the average diameter. In case of non-spherical, such as, for example, needle-like particles, the longest dimension (here the length) is used for determining the particle size.

The ratio of microwave active particles to fluorinated copolymer to be decomposed depends on the reactor type, dimension, and configuration. In some embodiments, the weight ratio of microwave active particles to fluorinated copolymer is from about 1:1,000 to about 1:0.1 or from about 1:10 to about 1:1.

The microwave active particles may be present, for example, in the carrier gas, reaction medium, or fluidised bed. This means the microwave active particles are in a mobile phase during the first heating and/or second heating. They may be introduced into the reactor through auxiliary gas streams simultaneously or non-simultaneously with the fluorinated copolymer, or they may be present in the reactor before the fluorinated copolymer is introduced into reactor. The microwave active particles may also be added to the fluorinated copolymer before, during, or after the fluorinated copolymer is fed into the reactor, or more specifically, into the decomposition zone. Alternatively, the microwave active particles may also be present in an immobile phase during the first and/or second heating, for example, in the same or similar way as catalytic beds. Some of the microwave particles may be removed from the reactor, for example, by the carrier gas, and may be replaced during at least one of the first heating or second heating. This can be done by continuous or discontinuous feeding.

The presence of microwave active particles in the decomposition zone of the reactor generates hot spots in the reaction mixture facilitating heat transfer from the reactor to the reaction mixture. This can lead to a faster heat transfer into the reaction mixture and/or a more homogeneous distribution of heat within the reaction mixture compared to reactors that are not heated by microwave irradiation, such as reactors heated through heat exchange, combustion, or electrical resistance. The presence of microwave active particles may also allow the process to be run more energy efficiently. It also allows for clearing more easily blocked reactors, for example, caused by unreacted or polymerized material through overfeeding, by the collapse of fluidised bed, and/or as a consequence of interrupting or terminating the decomposition reaction and/or shutting down the reactor.

The fluorinated copolymer useful in the process of the present disclosure may be included in a catalyst ink or polymer electrolyte membrane in a fuel cell or other electrolytic cell. A membrane electrode assembly (MEA) is the central element of a proton exchange membrane fuel cell, such as a hydrogen fuel cell. Fuel cells are electrochemical cells which produce usable electricity by the catalyzed combination of a fuel such as hydrogen and an oxidant such as oxygen. Typical MEA's comprise a polymer electrolyte membrane (PEM) (also known as an ion conductive membrane (ICM)), which functions as a solid electrolyte. One face of the PEM is in contact with an anode electrode layer and the opposite face is in contact with a cathode electrode layer. Each electrode layer includes electrochemical catalysts, typically including platinum metal. Gas diffusion layers (GDL's) facilitate gas transport to and from the anode and cathode electrode materials and conduct electrical current. The GDL may also be called a fluid transport layer (FTL) or a diffuser/current collector (DCC). The anode and cathode electrode layers may be applied to GDL's in the form of a catalyst ink, and the resulting coated GDL's sandwiched with a PEM to form a five-layer MEA. Alternately, the anode and cathode electrode layers may be applied to opposite sides of the PEM in the form of a catalyst ink, and the resulting catalyst-coated membrane (CCM) sandwiched with two GDL's to form a five-layer MEA. Details concerning the preparation of catalyst inks and their use in membrane assemblies can be found, for example, in U.S. Pat. Publ. No. 2004/0107869 (Velamakanni et al.). In a typical PEM fuel cell, protons are formed at the anode via hydrogen oxidation and transported across the PEM to the cathode to react with oxygen, causing electrical current to flow in an external circuit connecting the electrodes. The PEM forms a durable, non-porous, electrically non-conductive mechanical barrier between the reactant gases, yet it also passes $H^+$ ions readily.

A catalyst ink composition can include a fluorinated copolymer as described above in any of its embodiments combined with catalyst particles (e.g., metal particles or carbon-supported metal particles). A variety of catalysts may be useful. Typically, carbon-supported catalyst particles are used. Typical carbon-supported catalyst particles are 50% to 90% carbon and 10% to 50% catalyst metal by weight, the catalyst metal typically comprising platinum for the cathode and platinum and ruthenium in a weight ratio of 2:1 for the anode. However, other metals may be useful, for example, gold, silver, palladium, iridium, rhodium, ruthenium, iron, cobalt, nickel, chromium, tungsten, manganese, vanadium, and alloys thereof. To make an MEA or CCM, catalyst may be applied to the PEM by any suitable means, including both hand and machine methods, including hand brushing, notch bar coating, fluid bearing die coating, wire-wound rod coating, fluid bearing coating, slot-fed knife coating, three-roll coating, or decal transfer. Coating may be achieved in one application or in multiple applications. The catalyst ink may be applied to a PEM or a GDL directly, or the catalyst ink may be applied to a transfer substrate, dried, and thereafter applied to the PEM or to the FTL as a decal.

In some embodiments, the catalyst ink includes the fluorinated copolymer described above at a concentration of at least 10, 15, or 20 percent by weight and up to 30 percent by weight, based on the total weight of the catalyst ink. In some embodiment, the catalyst ink includes the catalyst particles in an amount of at least 10, 15, or 20 percent by weight and up to 50, 40, or 30 percent by weight, based on the total weight of the catalyst ink. The catalyst particles may be added to a fluoropolymer dispersion to make a catalyst ink. The resulting catalyst ink may be mixed, for example, with heating. The percent solid in the catalyst ink may be selected, for example, to obtain desirable rheological properties. Examples of suitable organic solvents useful for including in the catalyst ink include, lower alcohols (e.g., methanol, ethanol, isopropanol, n-propanol), polyols (e.g., ethylene glycol, propylene glycol, glycerol), ethers (e.g., tetrahydrofuran and dioxane), diglyme, polyglycol ethers, ether acetates, acetonitrile, acetone, dimethylsulfoxide (DMSO), N,N dimethyacetamide (DMA), ethylene carbonate, propylene carbonate, dimethylcarbonate, diethylcarbonate, N,N-dimethylformamide (DMF), N-methylpyrrolidinone (NMP), dimethylimidazolidinone, butyrolactone, hexamethylphosphoric triamide (HMPT), isobutyl methyl ketone, sulfolane, and combinations thereof. In some embodiments, the catalyst ink contains 0% to 50% by weight of a lower alcohol and 0% to 20% by weight of a polyol. In addition, the ink may contain 0% to 2% of a suitable dispersant.

In some embodiments, the fluorinated copolymer useful in the process of the present disclosure is included in a polymer electrolyte membrane. The copolymer may be formed into a polymer electrolyte membrane by any suitable method, including casting, molding, and extrusion. Typically, the membrane is cast from a fluoropolymer dispersion and then dried, annealed, or both. The copolymer may be cast from a suspension. Any suitable casting method may be used, including bar coating, spray coating, slit coating, and brush coating. After forming, the membrane may be annealed, typically at a temperature of 120° C. or higher, more typically 130° C. or higher, most typically 150° C. or higher. A polymer electrolyte membrane can be prepared by obtaining the copolymer in a fluoropolymer dispersion, optionally purifying the dispersion by ion-exchange purification, and concentrating the dispersion to make a membrane. Typically, if the fluoropolymer dispersion is to be used to form a membrane, the concentration of copolymer is advantageously high (e.g., at least 20, 30, or 40 percent by weight). Often a water-miscible organic solvent is added to facilitate film formation. Examples of water-miscible solvents include, lower alcohols (e.g., methanol, ethanol, isopropanol, n-propanol), polyols (e.g., ethylene glycol, propylene glycol, glycerol), ethers (e.g., tetrahydrofuran and dioxane), ether acetates, acetonitrile, acetone, dimethylsulfoxide (DMSO), N,N dimethyacetamide (DMA), ethylene carbonate, propylene carbonate, dimethylcarbonate, diethylcarbonate, N,N-dimethylformamide (DMF), N-methylpyrrolidinone (NMP), dimethylimidazolidinone, butyrolactone, hexamethylphosphoric triamide (HMPT), isobutyl methyl ketone, sulfolane, and combinations thereof.

Polymer electrolyte membranes can include a salt of at least one of cerium, manganese or ruthenium or one or more cerium oxide or zirconium oxide compounds is added to the acid form of the copolymer before membrane formation. Typically, the salt of cerium, manganese, or ruthenium and/or the cerium or zirconium oxide compound is mixed well with or dissolved within the copolymer to achieve substantially uniform distribution. The salt of cerium, manganese, or ruthenium may comprise any suitable anion, including chloride, bromide, hydroxide, nitrate, sulfonate, acetate, phosphate, and carbonate. More than one anion may be present. Other salts may be present, including salts that include other metal cations or ammonium cations. Once cation exchange occurs between the transition metal salt and the acid form of the ionomer, it may be desirable for the acid formed by combination of the liberated proton and the original salt anion to be removed. Thus, it may be useful to use anions that generate volatile or soluble acids, for example chloride or nitrate. Manganese cations may be in any suitable oxidation state, including $Mn^{2+}$, $Mn^{3+}$, and $Mn^{4+}$, but are most typically $Mn^{2+}$. Ruthenium cations may be in any suitable oxidation state, including $Ru^{3+}$ and $Ru^{4+}$, but are most typically $Ru^{3+}$. Cerium cations may be in any suitable oxidation state, including $Ce^{3+}$ and $Ce^{4+}$. Without wishing to be bound by theory, it is believed that the cerium, manganese, or ruthenium cations persist in the polymer electrolyte because they are exchanged with $H^+$ ions from the anion groups of the polymer electrolyte and become associated with those anion groups. Furthermore, it is believed that polyvalent cerium, manganese, or ruthenium cations may form crosslinks between anion groups of the polymer electrolyte, further adding to the stability of the polymer. In some embodiments, the salt may be present in solid form. The cations may be present in a combination of two or more forms including solvated cation, cation associated with bound anion groups of the polymer electrolyte membrane, and cation bound in a salt precipitate. The amount of salt added is typically between 0.001 and 0.5 charge equivalents based on the molar amount of acid functional groups present in the polymer electrolyte, more typically between 0.005 and 0.2, more typically between 0.01 and 0.1, and more typically between 0.02 and 0.05. Further details for combining an anionic copolymer with cerium, manganese, or ruthenium cations can be found in U.S. Pat. Nos. 7,575,534 and 8,628,871, each to Frey et al.

Polymer electrolyte membranes can also include cerium oxide compounds. The cerium oxide compound may contain cerium in the (IV) oxidation state, the (III) oxidation state, or both and may be crystalline or amorphous. The cerium oxide may be, for example, $CeO_2$ or $Ce_2O_3$. The cerium oxide may be substantially free of metallic cerium or may contain metallic cerium. The cerium oxide may be, for example, a thin oxidation reaction product on a metallic cerium particle. The cerium oxide compound may or may not contain other metal elements. Examples of mixed metal oxide compounds comprising cerium oxide include solid solutions such as zirconia-ceria and multicomponent oxide compounds such as barium cerate. Without wishing to be bound by theory, it is believed that the cerium oxide may strengthen the polymer by chelating and forming crosslinks between bound anionic groups. The amount of cerium oxide compound added is typically between 0.01 and 5 weight percent based on the total weight of the copolymer, more typically between 0.1 and 2 weight percent, and more typically between 0.2 and 0.3 weight percent. The cerium oxide compound is typically present in an amount of less than 1% by volume relative to the total volume of the polymer electrolyte membrane, more typically less than 0.8% by volume, and more typically less than 0.5% by volume. Cerium oxide may be in particles of any suitable size, in some embodiments, between 1 nm and 5000 nm, 200 nm to 5000 nm, or 500 nm to 1000 nm. Further details regarding polymer electrolyte membranes including cerium oxide compounds can be found in U.S. Pat. No. 8,367,267 (Frey et al.).

The polymer electrolyte membrane, in some embodiments, may have a thickness of up to 90 microns, up to 60 microns, or up to 30 microns. A thinner membrane may provide less resistance to the passage of ions. In fuel cell use, this results in cooler operation and greater output of usable energy. Thinner membranes must be made of materials that maintain their structural integrity in use.

In some embodiments, a fluorinated copolymer may be imbibed into a porous supporting matrix, typically in the form of a thin membrane having a thickness of up to 90 microns, up to 60 microns, or up to 30 microns. Any suitable method of imbibing the copolymer into the pores of the supporting matrix may be used, including overpressure, vacuum, wicking, and immersion. In some embodiments, the copolymer is embedded in the matrix upon crosslinking. Any suitable supporting matrix may be used. Typically the supporting matrix is electrically non-conductive. Typically, the supporting matrix is composed of a fluoropolymer, which is more typically perfluorinated. Typical matrices include porous polytetrafluoroethylene (PTFE), such as biaxially stretched PTFE webs. In another embodiment fillers (e.g. fibers) might be added to the polymer to reinforce the membrane.

To make an MEA, GDL's may be applied to either side of a CCM by any suitable means. Any suitable GDL may be used in the practice of the present disclosure. Typically, the GDL is comprised of sheet material comprising carbon fibers. Typically, the GDL is a carbon fiber construction selected from woven and non-woven carbon fiber constructions. Carbon fiber constructions which may be useful in the practice of the present disclosure may include Torayr™ Carbon Paper, SpectraCarb™ Carbon Paper, AFN™ non-woven carbon cloth, and Zoltek™ Carbon Cloth. The GDL may be coated or impregnated with various materials, including carbon particle coatings, hydrophilizing treatments, and hydrophobizing treatments such as coating with polytetrafluoroethylene (PTFE).

In use, the MEA is typically sandwiched between two rigid plates, known as distribution plates, also known as bipolar plates (BPP's) or monopolar plates. Like the GDL, the distribution plate is typically electrically conductive. The distribution plate is typically made of a carbon composite, metal, or plated metal material. The distribution plate distributes reactant or product fluids to and from the MEA electrode surfaces, typically through one or more fluid-conducting channels engraved, milled, molded or stamped in the surface(s) facing the MEA(s). These channels are sometimes designated a flow field. The distribution plate may distribute fluids to and from two consecutive MEA's in a stack, with one face directing fuel to the anode of the first MEA while the other face directs oxidant to the cathode of the next MEA (and removes product water), hence the term "bipolar plate." Alternately, the distribution plate may have channels on one side only, to distribute fluids to or from an MEA on only that side, which may be termed a "monopolar plate." A typical fuel cell stack comprises a number of MEA's stacked alternately with bipolar plates.

In some embodiments, the fluorinated copolymer useful in the process of the present disclosure is a component of a device comprising at least one of a catalyst ink, a polymer electrolyte membrane, a catalyst layer, a gas diffusion layer, or a bipolar plate as described above in any of their embodiments. Thus, the process of the present disclosure can be carried out on any of these devices.

Another type of electrochemical device is an electrolysis cell, which uses electricity to produce chemical changes or chemical energy. An example of an electrolysis cell is a chlor-alkali membrane cell where aqueous sodium chloride is electrolyzed by an electric current between an anode and a cathode. The electrolyte is separated into an anolyte portion and a catholyte portion by a membrane subject to harsh conditions. In chlor-alkali membrane cells, caustic sodium hydroxide collects in the catholyte portion, hydrogen gas is evolved at the cathode portion, and chlorine gas is evolved from the sodium chloride-rich anolyte portion at the anode. The fluorinated copolymer useful in the process of the present can be a component, for example, of a catalyst ink or electrolyte membranes for use in chlor-alkali membrane cells or other electrolytic cells.

The fluorinated copolymer useful in the process of the present disclosure may also be a component of a binder for an electrode in other electrochemical cells (for example, lithium ion batteries). To make electrodes, powdered active ingredients can be dispersed in a solvent with the copolymer and coated onto a metal foil substrate, or current collector. The resulting composite electrode contains the powdered active ingredient in the polymer binder adhered to the metal substrate. Useful active materials for making negative electrodes include alloys of main group elements and conductive powders such as graphite. Examples of useful active materials for making a negative electrode include oxides (tin oxide), carbon compounds (e.g., artificial graphite, natural graphite, soil black lead, expanded graphite, and scaly graphite), silicon carbide compounds, silicon-oxide compounds, titanium sulfides, and boron carbide compounds. Useful active materials for making positive electrodes include lithium compounds, such as $Li_{4/3}Ti_{5/3}O_4$, $LiV_3O_8$, $LiV_2O_5$, $LiCo_{0.2}Ni_{0.8}O_2$, $LiNiO_2$, $LiFePO_4$, $LiMnPO_4$, $LiCoPO_4$, $LiMn_2O_4$, and $LiCoO_2$. The electrodes can also include electrically conductive diluents and adhesion promoters.

Electrochemical cells can be made by placing at least one each of a positive electrode and a negative electrode in an electrolyte. Typically, a microporous separator can be used to prevent the contact of the negative electrode directly with the positive electrode. Once the electrodes are connected externally, lithiation and delithiation can take place at the electrodes, generating a current. A variety of electrolytes can be employed in a lithium-ion cell. Representative electrolytes contain one or more lithium salts and a charge-carrying medium in the form of a solid, liquid, or gel. Examples of lithium salts include $LiPF_6$, $LiBF_4$, $LiClO_4$, lithium bis (oxalato)borate, $LiN(CF_3SO_2)_2$, $LiN(C_2FSO_2)_2$, $LiAsF_6$, $LiC(CF_3SO_2)_3$, and combinations thereof. Examples of solid charge carrying media include polymeric media such as polyethylene oxide, polytetrafluoroethylene, polyvinylidene fluoride, fluorine-containing copolymers, polyacrylonitrile, combinations thereof, and other solid media that will be familiar to those skilled in the art. Examples of liquid charge carrying media include ethylene carbonate, propylene carbonate, dimethyl carbonate, diethyl carbonate, ethyl methyl carbonate, butylene carbonate, vinylene carbonate, fluoroethylene carbonate, fluoropropylene carbonate, gamma-butyrolactone, methyl difluoroacetate, ethyl difluoroacetate, dimethoxyethane, diglyme (bis(2-methoxyethyl) ether), tetrahydrofuran, dioxolane, combinations thereof and other media that will be familiar to those skilled in the art. Examples of charge carrying media gels include those described in U.S. Pat. No. 6,387,570 (Nakamura et al.) and 6,780,544 (Noh). The electrolyte can include other additives (e.g., a cosolvent or a redox chemical shuttle).

The electrochemical cells can be useful as rechargeable batteries and can be used in a variety of devices, including portable computers, tablet displays, personal digital assistants, mobile telephones, motorized devices (e.g., personal or household appliances and vehicles), instruments, illumination devices (e.g., flashlights) and heating devices. One or more of the electrochemical cells can be combined to provide battery pack.

In some embodiments, the fluorinated copolymer useful in the process of the present disclosure is a component of a device comprising at least one of a binder, electrolysis cell, or a battery as described above in any of their embodiments. Thus, the process of the present disclosure can be carried out on any of these devices.

When the fluorinated copolymer is a component of a device comprising at least one of a catalyst ink, a polymer electrolyte membrane, a catalyst layer, a gas diffusion layer, a bipolar plate, an electrolysis cell, or a redox flow battery, the process of the present disclosure can further comprise at least one crushing (e.g., milling or grinding) or shredding the device. The device (e.g., in particulate or shredded form) can also be heated while simultaneously heating the fluorinated copolymer.

Fluorinated copolymer as components of a device comprising at least one of a catalyst ink, a polymer electrolyte membrane, a catalyst layer, a gas diffusion layer, a bipolar plate, an electrolysis cell, or a redox flow battery can be in salt form. That is, the sulfonate and/or carboxylate groups may be in salt form. In some embodiments, it is useful for the fluorinated copolymer to include sulfonic acid groups or carboxylic acid groups instead of the salts. In some embodiments, the process of the present disclosure further comprises treating the fluorinated copolymer (e.g., in the presence or absence of any of the devices described above) with an inorganic acid (e.g., HF, hydrochloric acid, or sulfuric acid) to convert the fluorinated copolymer to its acid form, that is, including sulfonic acid groups or carboxylic acid groups.

The reactor useful for carrying out the process of the present disclosure may contain or may be connected to a plasma zone, where a plasma is generated. The plasma zone is typically located at or after the decomposition zone. The plasma may accelerate the decomposition reaction. When used after the decomposition zone, the plasma may prevent or reduce precipitation of fluorocarbon particles and repolymerization. A plasma involves the ionisation of a gas. Inside the plasma negatively and positively charged compounds are present in substantially equal amounts. A plasma may be generated, for example through, microwave irradiation, for example by increasing the energy of the microwave irradiation until a plasma state is reached and stabilized. A plasma may also be generated, for example, by electric arcs, such as described, for example, U.S. Pat. No. 7,252,744 (Van der Walt et al.), or by corona treatment. The energy level of the plasma zone is typically optimized to stabilize the plasma but to prevent or reduce the deposition of fluorocarbon particles by minimizing the decomposition of fluorinated olefins. The energy level required to generate and stabilize the plasma may depend on the composition and amounts of the product gas and if present carrier gas or gaseous reaction media.

The reactor useful for carrying out the process of the present disclosure may also contain or may be connected to a quenching zone. The quenching zone is located after the decomposition zone, and if a plasma zone is located after the decomposition zone, the quenching zone is typically located after the plasma zone. Hot product gas, generated by the first heating and second heating of the fluorinated copolymer and containing the fluorinated olefin can rapidly cooled (i.e., quenched) to stabilize the newly formed fluorinated olefins and preventing or reducing repolymerization. Typically quenching involves cooling the gas from a temperature of at least 550° C., in some embodiments, from about 600° C. to about 700° C., to a temperature below 250° C. in less than 5 seconds or less than 1 second. Any suitable quenching system may be used, for example, expansion of the product gas, gas quenching by means of another gas which is cold, quench probes, (e.g., those described in U.S. Pat. No. 7,252,744 (Van der Walt et al.)), or a combination thereof.

A range of fluorinated olefins and other fluorinated and non-fluorinated products may form from the process of the present disclosure and may be present in the product gas. The desired fluorinated olefins (e.g., at least one of TFE or HFP) may be separated by conventional gas separation systems, for example, condensation, expansion, and distillation. Therefore, in some embodiments, the process of the present disclosure further comprises separating TFE and/or HFP from the product gas.

Solid materials will typically stay in the bottom of the reactor or can be found/recovered from the quenching systems. Solid materials that are desirable to recover include metals (e.g., precious metals) from catalyst inks or catalyst layers graphite from bipolar plates, for example. In some embodiments, the process of the present disclosure further comprises recovering a metal after producing the fluorinated olefin. The metal can be a precious metal (e.g., gold, silver, platinum, or palladium).

As shown in the Examples, below, the process of the present disclosure carried out on an ionomer having an equivalent weight of 1100 provided 82% yield of TFE and HPF. By contrast, when this material was pyrolyzed at 620° C. in one step, a 20% yield of TFE/HIFP was observed.

In order that this disclosure can be more fully understood, the following examples are set forth. It should be understood that these examples are for illustrative purposes only and are not to be construed as limiting this disclosure in any manner.

EXAMPLES

In the following examples, the TFE/HFP yield was calculated on the theoretical possible amount of TFE/HFP subtracted by the measured gas volume after quenching. The yield was corrected with the results of analysis of the pyrolysis gases by gas chromatography (GC).

Reference Example 1

A free flowing, sintered PTFE-material with an average particle size of 850 prn was continuously fed (2 grams/minute) into a vertical fluidized bed reactor (58 mm height, 35 mm diameter). The reactor contained SiC particles and the fluidized bed was generated by feeding overheated steam into the reactor. The temperature in the reactor was maintained at 620° C. The hot pyrolysis gases were quenched with aqueous NaOH. The pyrolysis yield was 90% and 94% TFE; 5% HFP and 1% $C_4F_8$-cyclobutane were generated.

Control Example 2

A dried ionomner (based on TFE and $CF_2=CF-O-(CF_2)_4-SO_3Na$) with an equivalent weight of 1100 in the Na-form and a particle size of 1 mm was pyrolyzed as described in Example 1. The TFE/HFP yield was 21%; the ratio of TFE, HFP was 67% TFE and 33% HFP. Many unidentified gases were produced as observed by GC analysis.

Example 3

500 grams ionomer similar to Control Example 2 with EW 1100 and in the $SO_3H$-form was treated at 395° C. for 1 hour in an 4L-agitated bed reactor under a continuous steam flow. The ionomer-material showed a weight loss of 12%; indicating that $SO_3H$-groups were removed.

The temperature was then increased to 600° C. under a flow of overheated steam, the pyrolysis gases were quenched with aqueous KOH. The TFE/HFP pyrolysis yield after 3 hour (based on the pretreated ionomer) was 83%; 89% TFE and 11% HFP were generated. The unidentified products observed by GC in Control Example 2 were not observed in Example 3.

In this Example, weight loss was measured for a sample treated for 1 hour at 395° C. in a separate oven. There was not an interruption between the two steps.

In a separate experiment, the reaction in the agitated reactor was stopped after the 1-hour treatment at 395° C., and the remaining material was weighed to calculate the loss. Comparable results to Example 3 were obtained.

Various modifications and alterations of this disclosure may be made by those skilled in the art without departing from the scope and spirit of the disclosure, and it should be understood that this invention is not to be unduly limited to the illustrative embodiments set forth herein.

What is claimed is:

1. A process for producing a fluorinated olefin from a fluorinated copolymer comprising at least one of sulfonic acid groups, carboxylic acid groups, or salts thereof, the process comprising:
   heating the fluorinated copolymer at a first temperature not more than 450° C. to decompose the at least one of sulfonic acid groups, carboxylic acid groups, or salts thereof to form a partially pyrolyzed intermediate; and
   subsequently heating the partially pyrolyzed intermediate at a second temperature of at least 550° C. to produce the fluorinated olefin.

2. The process of claim 1, wherein the first temperature is in a range from 300° C. to 450° C., and wherein the second temperature is in a range from 600° C. to 700° C.

3. The process of claim 1, wherein the fluorinated copolymer comprises at least one of the sulfonic acid groups or carboxylic acid groups.

4. The process of claim 1, wherein the fluorinated copolymercomprises:
   divalent units represented by formula $-[CF_2-CF_2]-$; and divalent units independently represented by formula:

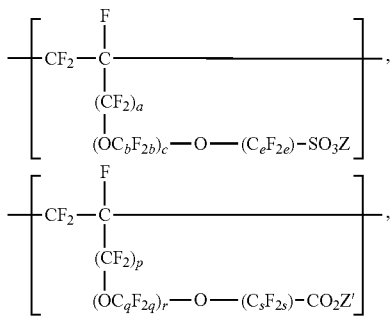

or combination thereof,
wherein a and p are each independently 0 to 2, each b and q is independently 2 to 8, each c and r is independently 0 to 2, each e and s is independently 1 to 8, and Z and Z' are each independently a hydrogen, an alkali-metal cation, or a quaternary ammonium cation.

5. The process of claim 4, wherein Z and Z' are each hydrogen.

6. The process of claim 5, further comprising combining the fluorinated copolymer with an inorganic acid.

7. The process of claim 4, wherein the fluorinated copolymer comprises divalent units represented by formula

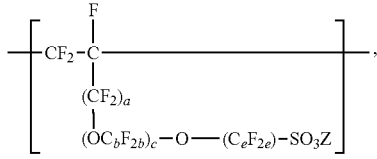

wherein a is 0 or 1, b is 2 or 3, c is 0 or 1, and e is 2 to 4.

8. The process of claim 4, wherein the fluorinated copolymer further comprises at least one divalent unit represented by formula

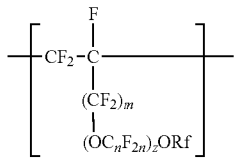

wherein Rf is a linear or branched perfluoroalkyl group having from 1 to 8 carbon atoms and optionally interrupted by one or more —O— groups, z is 0, 1, or 2, each n is independently 1, 2, 3, or 4, and m is 0, 1, or 2.

9. The process of claim 1, wherein the copolymer has an —$SO_3Z$ or —$CO_2Z'$ equivalent weight in a range from 500 to 2000, wherein Z and Z' are each independently a hydrogen, an alkali-metal cation, or a quaternary ammonium cation.

10. The process of claim 1, wherein the fluorinated olefin comprises at least one of tetrafluoroethylene or hexafluoropropylene.

11. The process of claim 1, wherein at least one of heating or subsequently heating is carried out at least partially with microwave radiation.

12. The process of claim 11, wherein at least one of the fluorinated copolymer or the partially pyrolyzed intermediate is contacted by microwave active particles.

13. The process of claim 1, wherein the fluorinated copolymer is a component of a device comprising at least one of a catalyst ink, a polymer electrolyte membrane, a catalyst layer, a gas diffusion layer, a bipolar plate, or an electrolysis cell.

14. The process of claim 13, further comprising at least one crushing or shredding the device and heating the device while simultaneously heating the fluorinated copolymer.

15. The process of claim 13, further comprising recovering a metal after producing the fluorinated olefin.

16. The process of claim 15, wherein the metal comprises at least one of gold, silver, platinum, or palladium.

17. The process of claim 1, wherein at least one of heating or subsequently heating is carried out in a fluidized bed reactor, agitated reactor, or rotary kiln.

18. The process of claim 1, wherein at least one of heating or subsequently heating is carried out in the presence of a carrier gas comprising at least one of nitrogen, steam, or a noble gas.

* * * * *